United States Patent
Betsugi

(10) Patent No.: US 11,642,187 B2
(45) Date of Patent: May 9, 2023

(54) SURGICAL INSTRUMENT, ASSEMBLY INCLUDING ADAPTOR AND SURGICAL INSTRUMENT, AND ROBOTIC SURGICAL SYSTEM

(71) Applicant: MEDICAROID CORPORATION, Kobe (JP)

(72) Inventor: Shota Betsugi, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 412 days.

(21) Appl. No.: 17/023,428

(22) Filed: Sep. 17, 2020

(65) Prior Publication Data
US 2021/0093403 A1    Apr. 1, 2021

(30) Foreign Application Priority Data
Sep. 27, 2019   (JP) .............................. JP2019-177054

(51) Int. Cl.
*A61B 34/37* (2016.01)
*A61B 90/50* (2016.01)
(Continued)

(52) U.S. Cl.
CPC .............. *A61B 34/37* (2016.02); *A61B 34/71* (2016.02); *A61B 90/50* (2016.02); *A61B 2034/301* (2016.02); *A61B 2034/305* (2016.02)

(58) Field of Classification Search
CPC ......... A61B 34/37; A61B 34/71; A61B 90/50; A61B 2034/301; A61B 2034/305;
(Continued)

(56) References Cited

U.S. PATENT DOCUMENTS

| 8,998,930 B2 | 4/2015 | Orban, III |
| 2008/0046122 A1* | 2/2008 | Manzo ................... A61B 90/98 700/245 |

(Continued)

FOREIGN PATENT DOCUMENTS

| EP | 2022416 A2 | 2/2009 |
| EP | 3616641 A1 | 3/2020 |

(Continued)

*Primary Examiner* — Tan-Uyen T Ho
*Assistant Examiner* — Regina Vahey
(74) *Attorney, Agent, or Firm* — Metrolex IP Law Group, PLLC

(57) ABSTRACT

A surgical instrument according to an embodiment may include: a base body including an attachment surface to be attached to the adaptor; an elongated shaft including one end connected to the base body; a treatment tool provided on a side of the other end of the shaft, elongate elements for operating the surgical tool, driven members rotatably provided on the base body and connected with end portions of the elongate elements; a holding member provided such that one end of each driven member is rotatably held by the base body and the other end of each driven member is rotatably held by the holding member; and a movable member provided movable with respect to the holding member and the base body and engageable with an adaptor. The movable member is configured, when moved with respect to the holding member and the base body, to be disengaged from the adaptor.

20 Claims, 12 Drawing Sheets

(51) Int. Cl.
*A61B 34/00* (2016.01)
*A61B 34/30* (2016.01)

(58) Field of Classification Search
CPC .......... A61B 2017/00477; A61B 34/30; A61B 2017/0046; A61B 2017/00464
See application file for complete search history.

(56) References Cited

U.S. PATENT DOCUMENTS

| | | |
|---|---|---|
| 2009/0030428 A1 | 1/2009 | Omori et al. |
| 2015/0257841 A1 | 9/2015 | Dachs, II |
| 2016/0361129 A1 | 12/2016 | Morrissette et al. |
| 2019/0000477 A1* | 1/2019 | Shelton, IV .......... A61B 17/29 |
| 2020/0069381 A1 | 3/2020 | Betsugi et al. |

FOREIGN PATENT DOCUMENTS

| | | |
|---|---|---|
| JP | 2009-045428 A | 3/2009 |
| JP | 2017-512525 A | 5/2017 |
| WO | 2016/176170 A1 | 11/2016 |
| WO | 2017/205311 A1 | 11/2017 |

* cited by examiner

SURGICAL INSTRUMENT, ASSEMBLY INCLUDING ADAPTOR AND SURGICAL INSTRUMENT, AND ROBOTIC SURGICAL SYSTEM

CROSS REFERENCE TO RELATED APPLICATIONS

This application claims priority to Japanese Patent Application No. 2019-177054 filed on Sep. 27, 2019, the entire contents of which are incorporated herein by reference.

BACKGROUND

The disclosure relates to a surgical instrument, and may particularly relate to a surgical instrument to be detachably connected to a robot arm of a robotic surgical system through an adaptor, an assembly including the adaptor and the surgical instrument, and a robotic surgical system including the robot arm, the adaptor, and the surgical instrument.

In a related art, there has been known a surgical instrument to be detachably connected to a robot arm of a robotic surgical system through an adaptor.

U.S. Pat. No. 8,998,930 discloses a surgical instrument including: a base body that includes tabs to be engaged with a holding member of an adaptor and that is attached to the adaptor; a surgical tool; an elongated shaft including one end connected to the base body and the other end connected to the surgical tool; and driven members that are rotatably provided on the base body and connected with end portions of elongate elements for operating the surgical tool. This surgical instrument is configured, when attaching the surgical instrument to the adaptor, to slide the base body with respect to the adaptor so as to engage the tabs of the base body with the holding member of the adaptor. The surgical instrument is further configured, when detaching the surgical instrument from the adaptor, to slide the surgical instrument with respect to the adaptor in a direction opposite to the attachment direction, so as to disengage the tabs of the base body from the holding member of the adaptor.

SUMMARY

However, in the surgical instrument disclosed in U.S. Pat. No. 8,998,930, when detaching the surgical instrument from the adaptor, the tabs of the base body are disengaged from the holding member of the adaptor by sliding the surgical instrument in the direction opposite to the attachment direction. Thus, in a case where an engagement force between the tabs and the holding member is large, a large force may be needed to disengage the surgical instrument from the adaptor when detaching the surgical instrument from the adaptor. In this case, easy attachment and detachment of the surgical instrument to and from the adaptor may not be realized. On the other hand, in a case where the engagement force between the tabs and the holding member is small, a force of fixing the surgical instrument to the adaptor may be small. In this case, stable fixing of the surgical instrument to the adaptor may not be realized. Accordingly, the surgical instrument disclosed in U.S. Pat. No. 8,998,930 may have difficulties in achieving both the easy attachment and detachment of the surgical instrument to and from the adaptor and the stable fixing of the surgical instrument to the adaptor.

An object of an embodiment of the disclosure may be directed to a surgical instrument that is to be detachably connected to a robot arm of a robotic surgical system through an adaptor, wherein the surgical instrument is capable of being easily attached to and detached from the adaptor and capable of being stably fixed to the adaptor.

A first aspect of the disclosure may be a surgical instrument to be detachably connected to a robot arm of a robotic surgical system through an adaptor. The surgical instrument includes: a base body including an attachment surface to be attached to the adaptor; an elongated shaft including one end connected to the base body and the other end; a treatment tool provided on a side of the other end of the shaft, elongate elements for operating the surgical tool, driven members rotatably provided in the base body and connected with end portions of the elongate elements; a holding member rotatably holding the driven members such that one end of each of the driven members is rotatably held by the base body and the other end of each of the driven members is rotatably held by the holding member; and a movable member provided to be movable with respect to the holding member and the base body and engaged with the adaptor. The movable member is configured, when moved with respect to the holding member and the base body, to be disengaged from the adaptor.

A second aspect of the disclosure may be an assembly including an adaptor and a surgical instrument. The adaptor is to be attached to a robot arm of a robotic surgical system and the surgical instrument is to be detachably connected to the adaptor. The surgical instrument includes: a base body including an attachment surface to be attached to the adaptor; an elongated shaft including one end connected to the base body and the other end; a treatment tool provided on a side of the other end of the shaft, elongate elements for operating the surgical tool, driven members rotatably provided on the base body and connected with end portions of the elongate elements; a holding member rotatably holding the driven members such that one end of each of the driven members is rotatably held by the base body and the other end of each of the driven members is rotatably held by the holding member; and a movable member provided movable with respect to the holding member and the base body and engaged with an adaptor. The movable member is configured, when moved with respect to the holding member and the base body, to be disengaged from the adaptor.

A third aspect of the disclosure may be a robotic surgical system that may include: a robot arm; an adaptor that is attached to the robot arm; and a surgical instrument that is detachably connected to the adaptor. The surgical instrument includes: a base body including an attachment surface to be attached to the adaptor; an elongated shaft including one end connected to the base body and the other end; a treatment tool provided on a side of the other end of the shaft, elongate elements for operating the surgical tool, driven members rotatably provided in the base body and connected with end portions of the elongate elements; a holding member rotatably holding the driven members such that one end of each of the driven members is rotatably held by the base body and the other end of each of the driven members is rotatably held by the holding member; and a movable member provided movable with respect to the holding member and the base body and engaged with an adaptor. The movable member is configured, when moved with respect to the holding member and the base body, to be disengaged from the adaptor.

DETAILED DESCRIPTION

Figure 1:
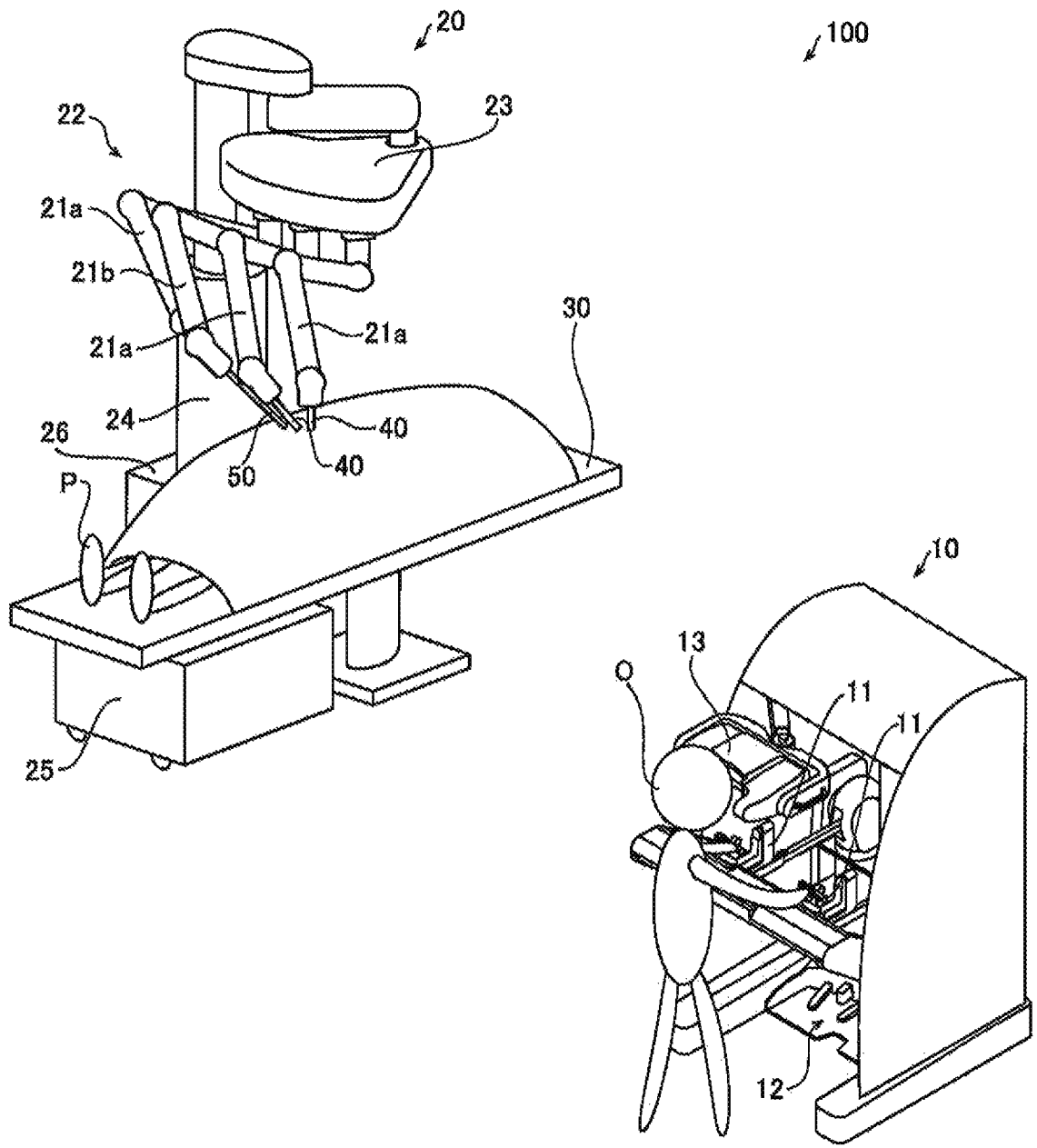
FIG. 1 is a diagram illustrating an overview of a robotic surgical system according to an embodiment.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

(Configuration of Robotic Surgical System)

A configuration of a robotic surgical system 100 according to an embodiment is described with reference to FIGS. 1 and 2.

As illustrated in FIG. 1, the robotic surgical system 100 includes a remote control apparatus 10 and a patient-side apparatus 20.

The remote control apparatus 10 is provided to remotely control medical equipment provided for the patient-side apparatus 20. When an operator O, as a surgeon, inputs an action mode instruction to be executed by the patient-side apparatus 20, to the remote control apparatus 10, the remote control apparatus 10 transmits the action mode instruction to the patient-side apparatus 20 through a controller 26. In response to the action mode instruction transmitted from the remote control apparatus 10, the patient-side apparatus 20 operates medical equipment such as surgical instruments 40, an endoscope 50, and the like, attached to robot arms 21a and 21b. This allows for minimally invasive surgery.

The patient-side apparatus 20 constitutes an interface to perform a surgery for a patient P. The patient-side apparatus 20 is positioned beside an operation table 30 on which the patient P is laid. The patient-side apparatus 20 includes plural robot arms 21a and 21b. One (21b) of the robot arms holds the endoscope 50 and the other robot arms 21a hold the surgical instruments 40. The robot arms 21a and 21b are commonly supported by a platform 23. Each of the robot arms 21a and 21b includes plural joints. Each joint includes a driver provided with a servo-motor and a position detector such as an encoder. The robot arms 21a and 21b are configured so that the medical equipment attached to each robot arm 21a and 21b is controlled by a driving signal given through the controller 26 and performs a desired movement.

The platform 23 is supported by a positioner 22 placed on the floor of an operation room. The positioner 22 includes a column 24 and a base 25. The column 24 includes an elevation shaft adjustable in the vertical direction. The base 25 includes wheels and is movable on the floor surface.

The surgical instruments 40 as the medical equipment is detachably attached to the distal ends of the robot arms 21a. Each surgical instrument 40 is detachably connected to the corresponding robot arm 21a of the robotic surgical system 100 through an adaptor 60 (see FIG. 3). As illustrated in FIG. 4, the surgical instrument 40 includes: a base body 40b including an attachment surface 40a to be attached to the adaptor 60; an elongated shaft 42 including one end thereof connected to the base body 40b and the other end thereof; and an end effector 41 provided on the other end side of the shaft 42. The end effector 41 is grasping forceps, scissors, a hook, a high-frequency knife, a snare wire, a clamp, or a stapler, for example. The end effector 41 is not limited to those and can be various types of treatment tools. In surgeries using the patient-side apparatus 20, the robot arms 21a introduce the surgical instruments 40 into the body of the patient P through a cannula (trocar) placed on the body surface of the patient P. The end effectors 41 of the surgical instruments 40 are then located near the surgery site. Note that the end effector 41 is an example of a surgical tool.

To the distal end of the robot arm 21b, the endoscope 50 as the medical equipment is detachably attached. The endoscope 50 captures an image in a body cavity of the patient P. The captured image is outputted to the remote control apparatus 10. The endoscope 50 is a 3D endoscope capable of capturing a three-dimensional image or a 2D endoscope. In surgeries using the patient-side apparatus 20, the robot arm 21b introduces the endoscope 50 into the body of the patient P through a trocar placed on the body surface of the patient P. The endoscope 50 is then located near the surgery site.

The remote control apparatus 10 constitutes the interface with the operator O. The remote control apparatus 10 is an apparatus that allows the operator O to operate the medical equipment attached to the robot arms 21a and 21b. Specifically, the remote control apparatus 10 is configured to transmit action mode instructions which are inputted by the operator O and are to be executed by the surgical instruments 40 and endoscope 50, to the patient-side apparatus 20 through the controller 26. The remote control apparatus 10 is installed beside the operation table 30 so that the operator O can see the condition of the patient P very well while operating the remote control apparatus 10, for example. The remote control apparatus 10 may be configured to transmit action mode instructions wirelessly and installed in a room different from the operation room where the operation table 30 is installed.

The action modes to be executed by the surgical instruments 40 include modes of actions to be taken by each surgical instrument 40 (a series of positions and postures) and actions to be executed by the function of each surgical instrument 40. When the surgical instrument 40 is a pair of grasping forceps, for example, the action modes to be executed by the surgical instrument 40 include roll and pitch positions of the wrist of the end effector 41 and actions to open and close the jaws. When the surgical instrument 40 is a high-frequency knife, the action modes to be executed by the surgical instrument 40 include vibration of the high-frequency knife, specifically, supply of current to the high-frequency knife. When the surgical instrument 40 is a snare wire, the action modes to be executed by the surgical instrument 40 include a capturing action and an action to release the captured object. Further the action modes may include an action to supply current to a bipolar or monopolar instrument to burn off the surgery site.

The action modes to be executed by the endoscope 50 include the position and posture of the tip of the endoscope 50 and setting of the zoom magnification, for example.

Figure 2:
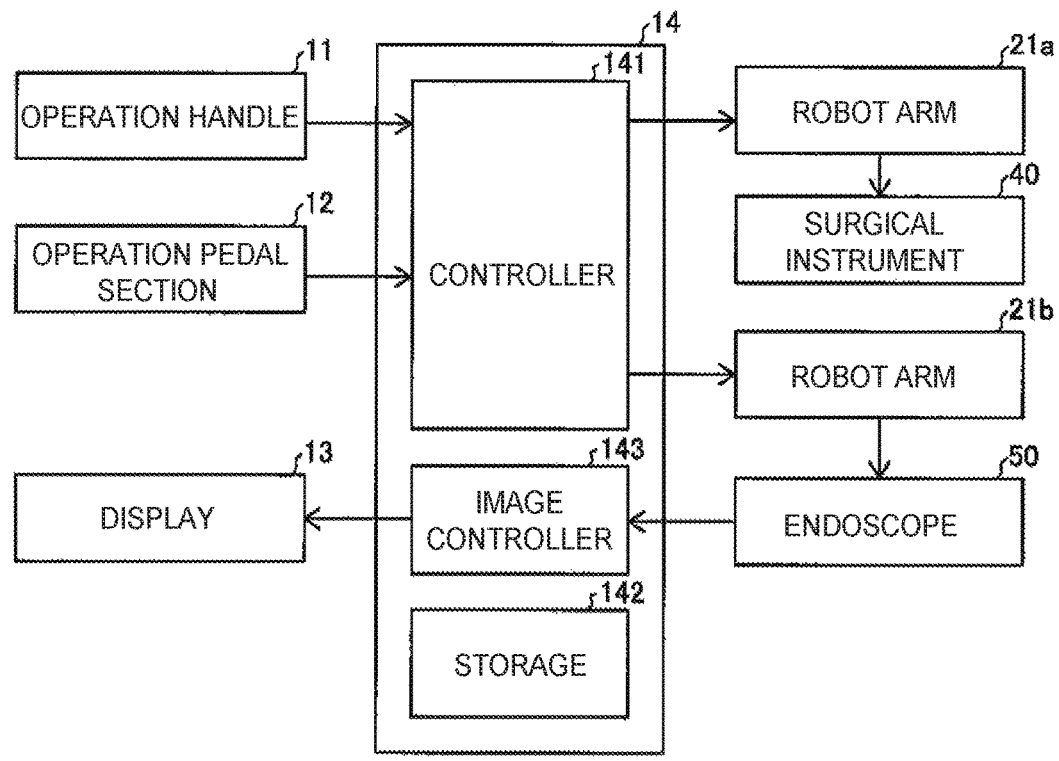
FIG. 2 is a block diagram illustrating a view of a control-related configuration of the robotic surgical system according to an embodiment.

As illustrated in FIGS. 1 and 2, the remote control apparatus 10 includes operation handles 11, an operation pedal section 12, a display section 13, and a control apparatus 14.

The operation handles 11 are provided in order to remotely operate the medical equipment attached to the robot arms 21a and 21b. Specifically, the operation handles 11 accept operations by the operator O for operating the medical equipment (the surgical instruments 40 and endoscope 50). The operation handles 11 include two operation handles 11 arranged side by side in the horizontal direction. One of the two operation handles 11 is operated by the right hand of the operator O while the other operation handle 11 is operated by the left hand of the operator O.

The operation handles 11 extend from the rear side of the remote control apparatus 10 toward the front side. The operation handles 11 are configured to move in a predetermined three-dimensional operation region. Specifically, the operation handles 11 are configured so as to move up and down, right and left, and forward and rearward.

The remote control apparatus 10 and patient-side apparatus 20 constitute a master-slave system in terms of controlling movement of the robot arms 21a and robot arm 21b. The operation handles 11 constitute an operating section or an operating part on the master side in the master-slave system, and the robot arms 21a and 21b holding the medical equipment constitute an operating section or an operation part on the slave side. When the operator O operates the operation handles 11, the movement of one of the robot arms 21a or 21b is controlled so that the distal end portion (the end effector 41 of the surgical instrument 40) of the robot arm 21a or the distal end portion (the endoscope 50) of the robot arm 21b moves following the movement of the operation handles 11.

The patient-side apparatus 20 controls the movement of the robot arms 21a in accordance with the set motion scaling ratio. When the motion scaling ratio is set to ½, for example, the end effectors 41 of the surgical instruments 40 move ½ of the movement distance of the operation handles 11. This allows for precise fine surgery.

The operation pedal section 12 or an operation pedal unit includes plural pedals to execute medical equipment-related functions. The plural pedals include a coagulation pedal, a cutting pedal, a camera pedal, and a clutch pedal. The plural pedals are operated by a foot of the operator O.

The coagulation pedal enables the surgical instrument 40 to coagulate a surgery site. Specifically, when the coagulation pedal is operated, voltage for coagulation is applied to the surgical instrument 40 to coagulate a surgery site. The cutting pedal enables the surgical instrument 40 to cut a surgery site. Specifically, the cutting pedal is operated to apply voltage for cutting to the surgical instrument 40 and cut a surgery site.

The camera pedal is used to control the position and orientation of the endoscope 50 that captures images within the body cavity. Specifically, the camera pedal enables operation of the endoscope 50 by the operation handles 11. That is, the position and orientation of the endoscope 50 are controllable by the operation handles 11 while the camera pedal is being pressed. The endoscope 50 is controlled by using both of the right and left operation handles 11, for example. Specifically, when the operator O rotates the right and left operation handles 11 about the middle point between the right and left operation handles 11, the endoscope 50 is rotated. When the operator O presses the right and left operation handles 11 together, the endoscope 50 goes forward into the body cavity. When the operator O pulls the right and left operation handles 11 together, the endoscope 50 goes back. When the operator O moves the right and left operation handles 11 together up, down, right, or left, the endoscope 50 moves up, down, right, or left, respectively.

The clutch pedal is used to temporarily disconnect operation-related connection between the operation handles 11 and the robot arms 21a to stop movement of the surgical instruments 40. Specifically, when the clutch pedal is being pressed, the robot arms 21a of the patient-side apparatus 20 do not work even if the operation handles 11 are operated. For example, when the operation handles 11 are operated and moved to the edge of the range of movement, the operator O operates the clutch pedal to temporarily disconnect the operation-related connection and then returns the operation handles 11 to the center of the range of movement. When the operator O stops operating the clutch pedal, the operation handles 11 are again connected to the robot arms 21a. The operator O restarts the operation for the operation handles 11 around the center thereof.

The display section 13 or a display unit is configured to display images captured by the endoscope 50. The display section 13 includes a scope type display section or a non-scope type display section. The scope type display section is a display section that the operator O looks into. The non-scope type display section is an open-type display section that includes a flat screen and the operator O is able to see without looking into, such as normal displays for personal computers.

When the scope type display section is attached, the scope type display section displays 3D images captured by the endoscope 50 attached to the robot arm 21b of the patient-side apparatus 20. When the non-scope type display section is attached, the non-scope type display section also displays 3D images captured by the endoscope 50 provided for the patient-side apparatus 20. The non-scope type display section may display 2D images captured by the endoscope 50 provided for the patient-side apparatus 20.

As illustrated in FIG. 2, the control apparatus 14 includes a controller 141, a storage 142, and an image controller 143, for example. The controller 141 includes a calculator such as a CPU. The storage 142 includes a memory, such as a ROM and a RAM. The control apparatus 14 may be composed of a single controller performing centralized control or may be composed of plural controllers that perform decentralized control in cooperation with each other. The controller 141 determines whether an action mode instruction inputted by the operation handles 11 is to be executed by the robot arms 21a or to be executed by the endoscope 50, depending on the state of the operation pedal section 12. When determining that the action mode instruction inputted by the operation handles 11 is to be executed by any one of the surgical instruments 40, the controller 141 transmits the action mode instruction to the corresponding robot arm 21a. The robot arm 21a is thereby driven for controlling movement of the surgical instrument 40 attached to the robot arm 21a.

When determining that the action mode instruction inputted by the operation handles 11 is to be executed by the endoscope 50, the controller 141 transmits the action mode instruction to the robot arm 21b. The robot arm 21b is thereby driven for control of movement of the endoscope 50 attached to the robot arm 21b.

The storage 142 stores control programs corresponding to the types of the surgical instrument 40, for example. The controller 141 reads the stored control programs according to the types of the attached surgical instruments 40. The action mode instructions from the operation handles 11 and/or the operation pedal section 12 of the remote control apparatus 10 thereby cause the respective surgical instruments 40 to perform proper movements.

The image controller 143 transmits images acquired by the endoscope 50 to the display section 13. The image controller 143 performs processing and modifying the images when needed.

(Configurations of Adaptor and Surgical Instrument)

With reference to FIGS. 3 to 15, the configurations of an adaptor 60 and the surgical instrument 40 according to an embodiment are described.

Figure 3:
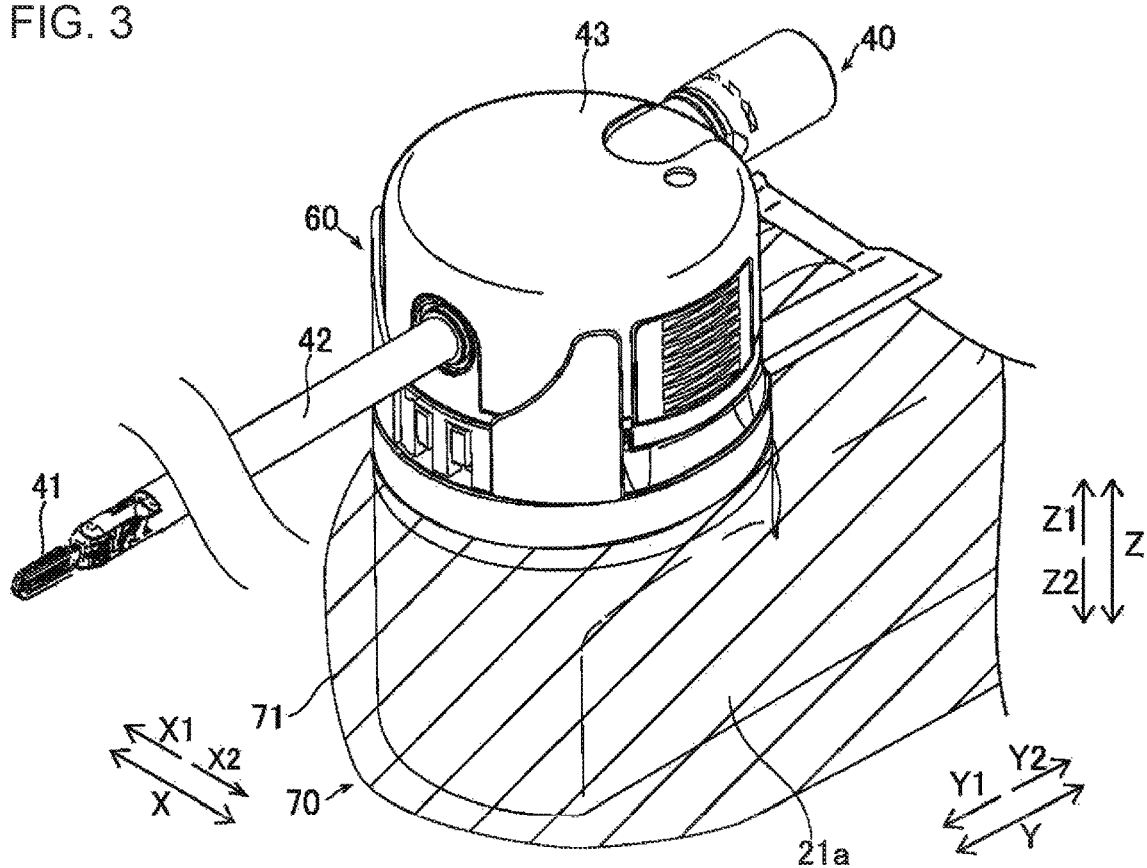
FIG. 3 is a diagram illustrating a perspective view of a state of an embodiment where a surgical instrument is attached to a robot arm through an adaptor.
Figure 4:
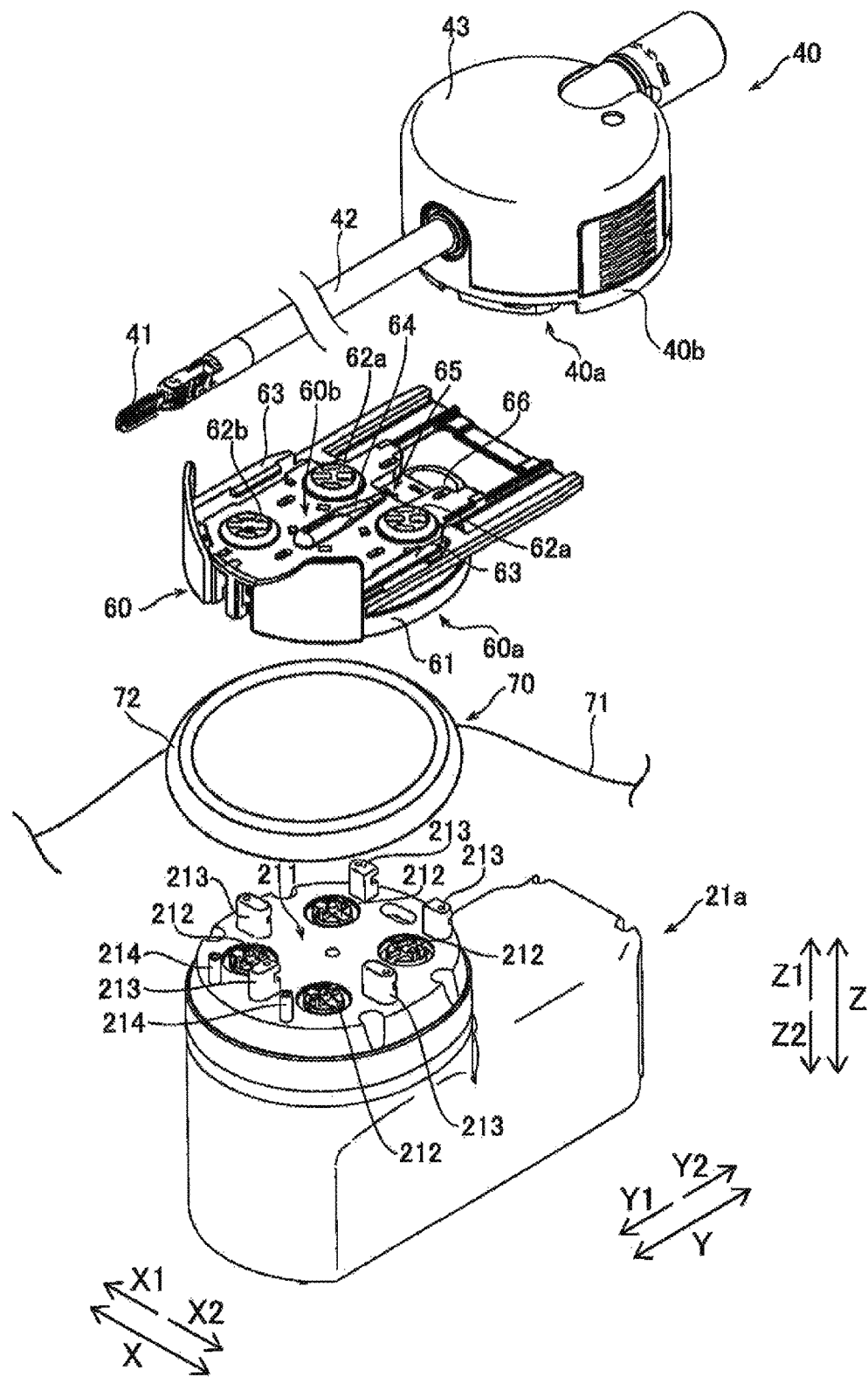
FIG. 4 is a diagram illustrating a perspective view of a state of an embodiment where the adaptor and the surgical instrument are detached from the robot arm.

As illustrated in FIG. 3, each of the robot arms 21a is used in a clean area and is covered with a drape 70. In operation rooms, clean technique is used in order to prevent surgical incision sites and the medical equipment from being contaminated by pathogen, foreign matters, or the like. The clean technique defines a clean area and a contaminated area, which is other than the clean area. The surgery sites are located in the clean area. Members of the surgical team, including the operator O, make sure that only sterile objects are placed in the clean area during surgery and perform sterilization for an object which is to be moved to the clean area from the contaminated area. Similarly, when the members of the surgical team including the operator O place their hands in the contaminated area, the members sterilize their hands before directly touching objects located in the clean area. Instruments used in the clean area are sterilized or are covered with sterile drape 70.

The drape 70 is arranged between the robot arm 21a and the surgical instrument 40. Specifically, the drape 70 is arranged between the adaptor 60 and the robot arm 21a. Further, the drape 70 is arranged between the robot arm 21b and the endoscope 50. The adaptor 60 is attached to the robot arm 21a while putting the drape 70 between the adaptor 60 and the robot arm 21a. Specifically, the adaptor 60 is a drape adaptor that puts the drape 70 between the adaptor 60 and the robot arm 21a. The surgical instrument 40 is attached to the adaptor 60 that is attached to the robot arm 21a with the drape 70 interposed therebetween. The robot arm 21a transmits driving force to the surgical instrument 40 through the adaptor 60 to drive the end effector 41 of the surgical instrument 40.

Figure 5:
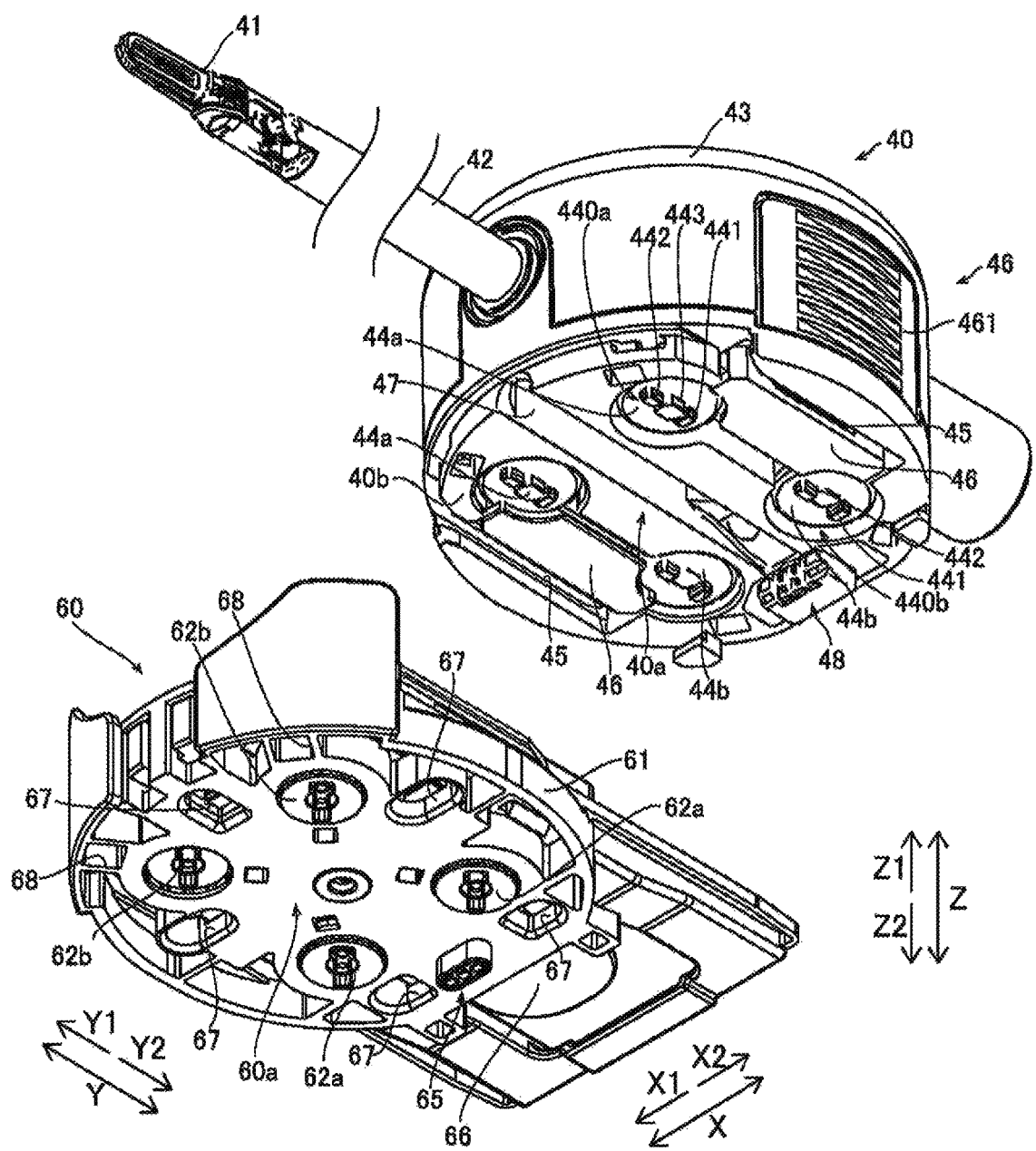
FIG. 5 is a diagram illustrating a perspective view of the surgical instrument and the adaptor according to an embodiment as seen from below.

As illustrated in FIG. 4, the adaptor 60 includes a base body 61, drive transmission members 62a and 62b, a pair of guide rails 63, a precedence guide rail 64, an electrode array 65, and an arm engagement portion 66. As illustrated in FIG. 5, the adaptor 60 includes arm engagement holes 67 and positioning holes 68. As illustrated in FIG. 4, of the drive transmission members 62a and 62b, the drive transmission members 62a are arranged in the Y2 side and the drive transmission members 62b are arranged in the Y1 side. In the adaptor 60, a first surface 60a is arranged in the Z2 side and attached to the robot arm 21a. The adaptor 60 includes a second surface 60b arranged in the Z1 side to which the surgical instrument 40 is attached.

The surgical instrument 40 is a surgical instrument that is detachably connected to the robot arm 21a of the robotic surgical system 100 through the adaptor 60. As illustrated in FIG. 5, an attachment surface 40a arranged in the Z2 side of the housing 43 of the surgical instrument 40 is attached to the adaptor 60. The surgical instrument 40 includes: plural driven members 44a and 44b; a pair of guide grooves 45; a pair of movable members 46; a precedence guide groove 47; and an electrode array 48. Of the driven members 44a and 44b, the driven members 44a are provided on the Y1 side and the driven member 44b are provided on the Y2 side. The surgical instrument 40 includes a base body 40b that includes the attachment surface 40a relative to the adaptor 60.

As illustrated in FIG. 4, the drape 70 includes a body part 71 and an attachment section 72. The body part 71 is made in a film form. The attachment section 72 is made by resin molding. The attachment section 72 includes a through-opening at a portion where the robot arm 21a is engaged with the adaptor 60. The through-opening may be provided corresponding to each of plural engagement portions. The through-openings may be provided corresponding to the plural engagement portions.

The adaptor 60 is attached to an adaptor attachment surface 211 of the robot arm 21a. The robot arm 21a includes rotation drive parts 212, engagement portions 213, and bosses 214.

As illustrated in FIG. 5, the driven members 44a and 44b of the surgical instrument 40 are driven to be rotated and thus drive the end effector 41. Specifically, one end (an end portion on the Y2 side) of the shaft 42 is connected to the base body 40b, and the other end (an end portion on the Y1 side) of the shaft 42 is connected to the end effector 41. The driven members 44a and 44b are connected to the end effector 41 with wires 421 (see FIG. 9) inserted through the shaft 42. Specifically, the driven members 44a and 44b are rotatably provided in the base body 40b. End portions of the wires 421 for operating the end effector 41 are connected to the driven members 44a and 44b, respectively. With the driven members 44a and 44b being rotated, the wires 421 are drawn to drive the end effector 41. In the housing 43, the driven members 44a and 44b are connected to the shaft 42 through gears. Specifically, the housing 43 is provided on the base body 40b to cover the driven members 44a and 44b. With the driven members 44a and 44b being rotated, the shaft 42 is rotated. The wires 421 are an example of elongate elements. The elongate elements may be cables, rods, or bunds, or the like.

As illustrated in FIG. 5, for example, the number of the driven members 44a is two, and the number of the driven members 44b is two. With one of the driven members 44a being rotated, the shaft 42 is rotated. With one or more of the other three driven members 44a and 44b being rotated, the end effector 41 is driven. The four driven members 44a and 44b are arranged such that two rows of them are arranged in the X direction while two columns of them are arranged in the Y direction.

Figure 6:
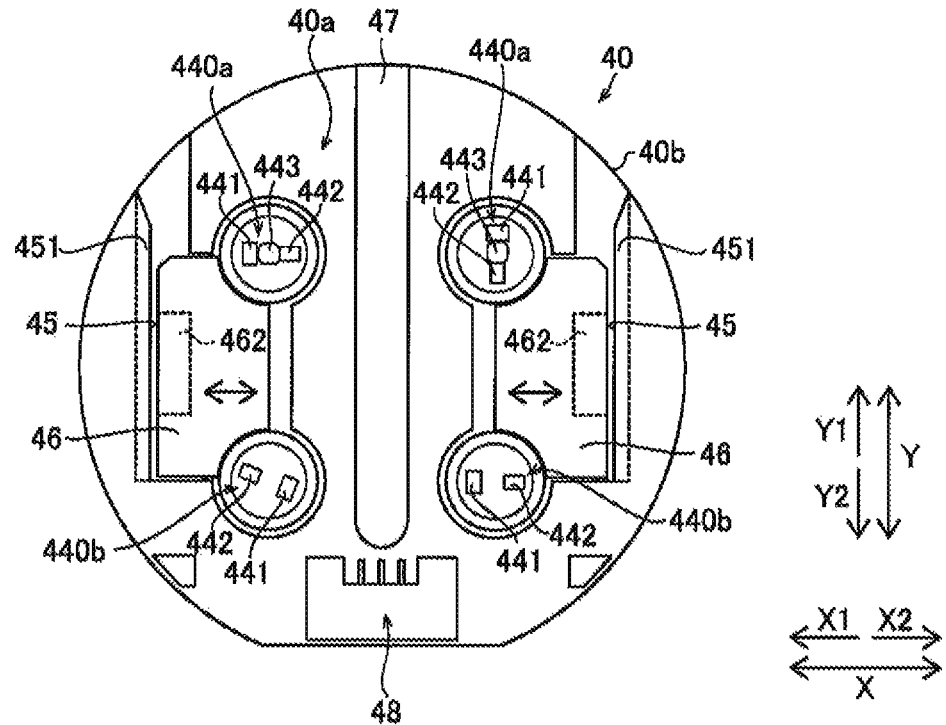
FIG. 6 is a diagram illustrating a view of an attachment surface of the surgical instrument according to an embodiment as seen from below.

As illustrated in FIGS. 5 and 6, each of the driven members 44a includes an engagement portion 440a that is engaged with the corresponding drive transmission member 62b provided in the adaptor 60. Each of the driven members 44b includes an engagement portion 440b that is engaged with the corresponding drive transmission member 62a provided in the adaptor 60. The engagement portion 440a is provided at the driven member 44a provided on the upstream side of the slide insertion direction (the Y1 side). The engagement portion 440b is provided at the driven member 44b provided on the downstream side of the slide insertion direction (the Y2 side). The engagement portion 440a and the engagement portion 440b have different shapes.

Specifically, the engagement portion 440a includes a first projection 441, a second projection 442 provided separately from the first projection 441, and a third projection 443 arranged between the first projection 441 and the second projection 442. The engagement portion 440b includes no third projection 443 but the first projection 441 and the second projection 442.

The pair of guide grooves 45 are provided on the attachment surface 40a of the base body 40b. The pair of guide grooves 45 is provided for slidably receiving the pair of guide rails 63 provided on the adaptor 60. Each of the guide grooves 45 is provided to extend along the Y direction. The pair of guide grooves 45 are provided to be opposed to each other in the X direction. The pair of guide grooves 45 are provided substantially parallel to each other. With the pair of guide rails 63 of the adaptor 60 being inserted in the pair of guide grooves 45, the pair of guide grooves 45 guide the attachment to the adaptor 60.

At least a part of each of the guide grooves 45 is defined by the corresponding one of the movable members 46. Specifically, the guide groove 45 is defined by the base body 40b and the corresponding movable member 46. The movable members 46 are movably provided with respect to the base body 40b and the holding member 49 (see FIG. 9). The movable member 46 is configured to release the engagement with the adaptor 60 by moving with respect to the base body 40b and the holding member 49. The movable members 46 are configured to change the groove widths of the guide grooves 45, by moving the movable members 46 with respect to the base body 40b and the holding member 49. Specifically, the width of each guide groove 45 is varied according to movement in the X direction of the corresponding movable member 46. Specifically, when the movable member 46 is moved inward, the width of the guide groove 45 is increased. When the movable member 46 is moved outward, the width of the guide groove 45 is decreased. The movable member 46 is biased to a direction (an outward direction) in which the width of the guide groove 45 is decreased.

The groove widths of the guide grooves 45 can be varied by moving the movable members 46. Consequently, it is possible to easily attach and detach the surgical instrument 40 to and from the adaptor 60 by sliding the guide grooves 45 having the increased groove widths with respect to the guide rails 63 of the adaptor 60. Additionally, the base body 40b of the surgical instrument 40 can be engaged with and fixed to the adaptor 60 by decreasing the groove widths of the guide grooves 45 after inserting the guide rails 63 of the adaptor 60 in the guide grooves 45. Consequently, it is possible to stably fix the surgical instrument 40 to the adaptor 60. Therefore, in the surgical instrument 40, which is to be detachably connected to the robot arm 21a of the robotic surgical system 100 through the adaptor 60, can be easily attached to and detached from the adaptor 60 and can be stably fixed to the adaptor 60.

The precedence guide groove 47 is provided to extend along the Y direction. The precedence guide groove 47 is provided between the pair of guide grooves 45. The precedence guide groove 47 is formed to extend substantially parallel to the pair of guide grooves 45. The precedence guide groove 47 is provided in the substantial center in the X direction of the attachment surface 40a.

The electrode array 48 is connected to the robot arm 21a through the electrode array 65 of the adaptor 60. The electrode array 48 is connected to a board provided in the housing 43. Specifically, the board of the surgical instrument 40 is connected to the robot arm 21a by attaching the surgical instrument 40 to the robot arm 21a through the adaptor 60. The board in the housing 43 is used for, for example, managing types of the surgical instrument 40 and the number of uses of the surgical instrument 40.

As illustrated in FIG. 4, the adaptor 60 is provided to detachably connect the surgical instrument 40 to the robot arm 21a of the robotic surgical system 100.

The drive transmission members 62a and 62b are rotatably provided to the base body 61 of the adaptor 60. Specifically, the drive transmission members 62a and 62b are provided to be rotatable about rotational axes thereof extending in the Z direction. The drive transmission members 62a and 62b transmit driving force of the rotation drive parts 212 of the robot arm 21a to the driven members 44b and 44a of the surgical instrument 40. The plural drive transmission members 62a and 62b are provided corresponding to the driven members 44b and 44a of the surgical instrument 40. The plural drive transmission members 62a and 62b are respectively arranged in positions corresponding to the driven members 44b and 44a of the surgical instrument 40.

Figure 7:
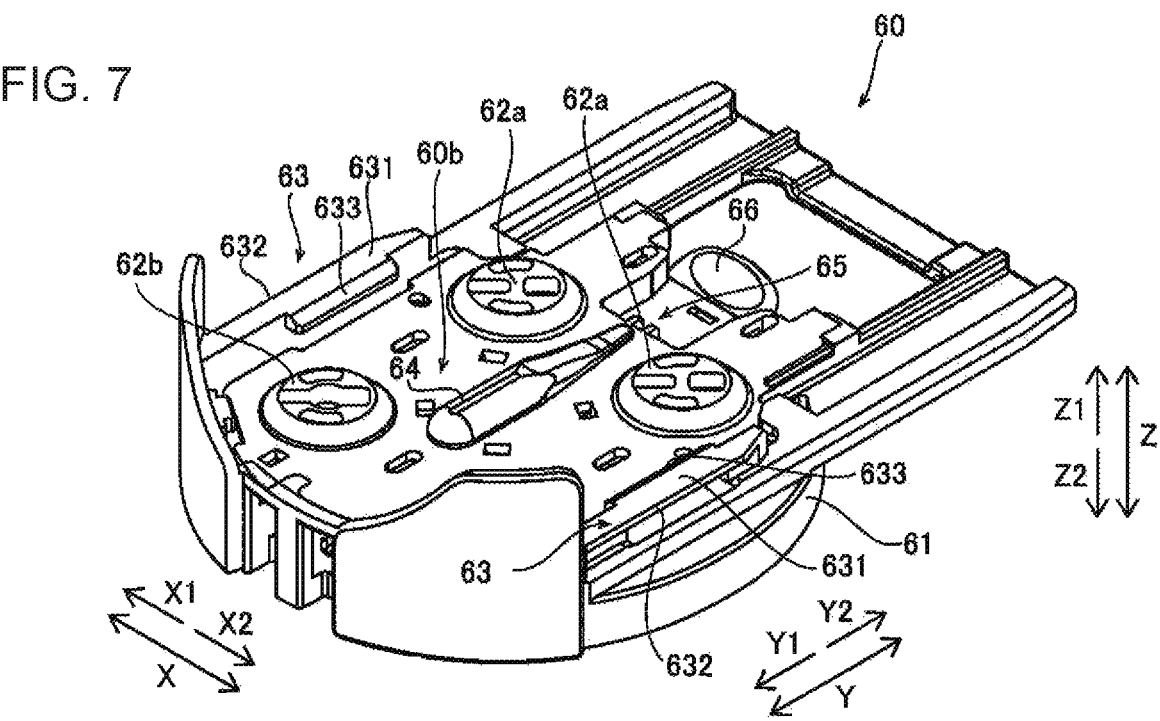
FIG. 7 is a diagram illustrating a perspective view of the adaptor according to an embodiment as seen from above.

As illustrated in FIG. 7, the guide rails 63 are provided on the second surface 60b of the adaptor 60. The guide rails 63 are provided to extend along the Y direction. The pair of guide rails 63 are provided to be opposed to each other in the X direction. The pair of guide rails 63 are provided corresponding to the pair of guide grooves 45 that are provided substantially parallel to each other on the attachment surface 40a of the surgical instrument 40. The pair of guide rails 63 of the second surface 60b are configured to receive the of guide pair of guide grooves 45 of the attachment surface 40a to slide the surgical instrument 40 in the Y direction so as to guide the surgical instrument 40 to a position where the drive transmission members 62a and 62b correspond to the driven members 44b and 44a provided on the attachment surface 40a.

The precedence guide rail 64 is provided on the second surface 60b of the adaptor 60. The precedence guide rail 64 is provided to extend along the Y direction. The precedence guide rail 64 is provided between the pair of guide rails 63. The precedence guide rail 64 is formed to extend substantially parallel to the pair of guide rails 63. The precedence guide rail 64 is provided in the substantial center in the X direction of the second surface 60b. The precedence guide rail 64 is provided corresponding to the precedence guide groove 47 provided on the attachment surface 40a. That is, the precedence guide rail 64 guides the surgical instrument 40 before the pair of guide rails 63 guide the surgical instrument 40.

The electrode array 65 is connected to the electrode array 48 of the surgical instrument 40 and the robot arm 21a.

As illustrated in FIGS. 4 and 5, the arm engagement portion 66 is engaged with the engagement portions 213 of the robot arm 21a. Specifically, the arm engagement portion 66 is engaged with the engagement portions 213 that are inserted in the arm engagement holes 67 provided in the first surface 60a. The arm engagement portion 66 can be moved in the Y direction. The arm engagement portion 66 is biased in the Y1 direction by a bias member. The engagement of the arm engagement portion 66 with the engagement portions 213 is made by moving the arm engagement portion 66 in the Y1 direction. On the other hand, the engagement of the arm engagement portion 66 with the engagement portions 213 is released by moving the arm engagement portion 66 in the Y2 direction.

The number of the arm engagement holes 67 provided is plural. That is, the adaptor 60 is fixed to the robot arm 21a by engagement of plural portions. For example, the number of the plurality of arm engagement holes 67 is five. The arm engagement holes 67 are provided at equal intervals along a circumferential direction of the first surface 60a.

The positioning holes 68 are provided in the first surface 60a. The bosses 214 of the robot arm 21a are fitted to the positioning holes 68. The number of the positioning holes 68 provided is plural. The positioning holes 68 are provided near an end portion in the Y1 side of the first surface 60a.

As illustrated in FIG. 7, each guide rail 63 includes a rail portion 631, a jut portion 632, and a tab portion 633. The rail portion 631 is formed to extend in the Y direction. The rail portion 631 is inserted into the guide groove 45 of the surgical instrument 40 and guides the movement of the surgical instrument 40 with respect to the adaptor 60.

The jut portion 632 is formed to jut in the X direction from the rail portion 631. Specifically, the jut portion 632 of the guide rails 63 on the X1 side is provided on the X1 side of the rail portion 631. The jut portion 632 of the guide rail 63 on the X2 side is provided on the X2 side of the rail portion 631.

The tab portion 633 is formed to jut in the X direction from the rail portion 631. Specifically, the tab portion 633 of the guide rail 63 on the X1 side is provided on the X2 side of the rail portion 631. The tab portion 633 of the guide rails 63 on the X2 side is provided on the X1 side of the rail portion 631. That is, the jut portion 632 is provided to the rail portion 631 on the opposite side of the tab portion 633. The jut portion 632 is provided on the outer side in the X direction of the rail portion 631. The tab portion 633 is provided on the inner side in the X direction of the rail portion 631.

The jut portion 632 is engaged with a restriction portion 451 (see FIG. 14) provided in the guide groove 45 of the surgical instrument 40. The engagement of the jut portion 632 with the restriction portion 451 enables rigid connection between the surgical instrument 40 and the adaptor 60 and prevents detachment of the surgical instrument 40 from the adaptor 60 in the Z direction.

Figure 14:
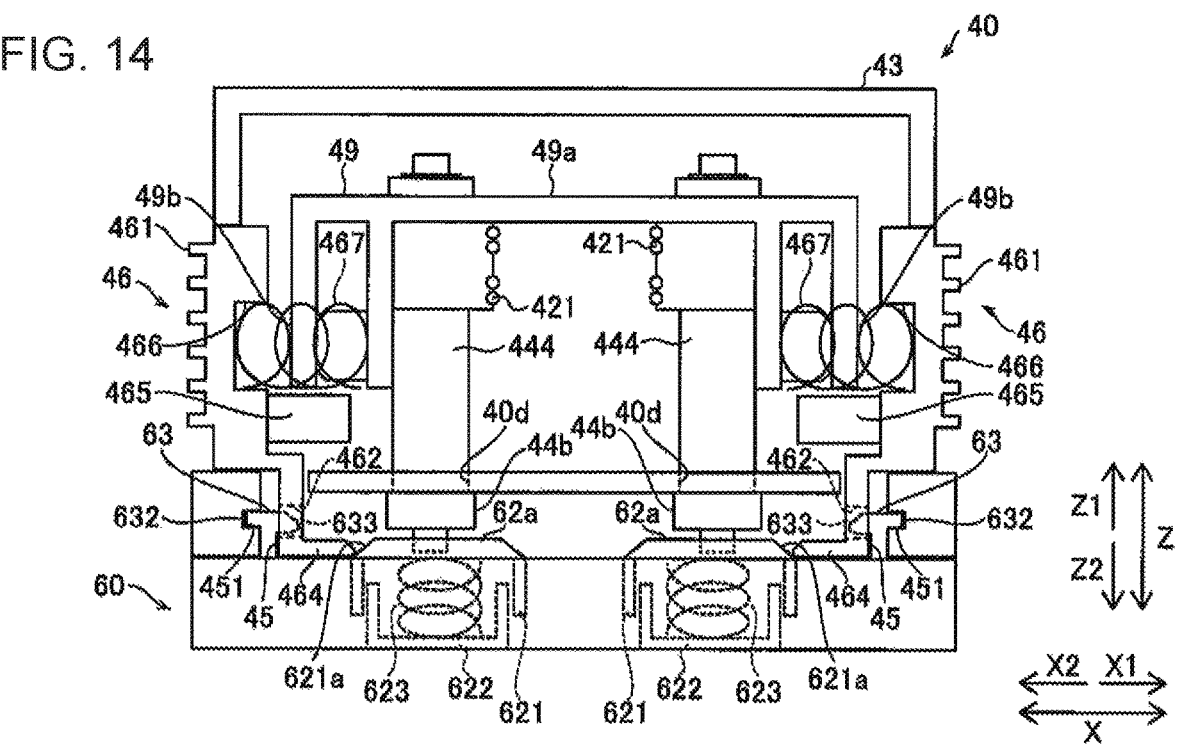
FIG. 14 is a diagram illustrating a first explanatory view for explaining movement of the movable member of the surgical instrument according to an embodiment.

The tab portion 633 is engaged with an engagement hole 462 (see FIG. 14) provided in the guide groove 45 of the surgical instrument 40. Specifically, the tab portion 633 is engaged with the engagement hole 462 provided in a side wall 463 of the movable member 46 forming the guide groove 45. Accordingly, the engagement of the tab portion 633 with the engagement hole 462 enables positioning and fixing of the surgical instrument 40 guided by the guide rail 63 with respect to the adaptor 60. That is, the engagement of the tab portion 633 with the engagement hole 462 enables positioning of the surgical instrument 40 in the Y direction with respect to the adaptor 60 and fixing (locking) of the surgical instrument 40 to the adaptor 60 to prevent detachment of the surgical instrument 40 in the Y direction. As illustrated in FIG. 14, the tab portion 633 is formed to be inclined along the X direction.

Figure 8:
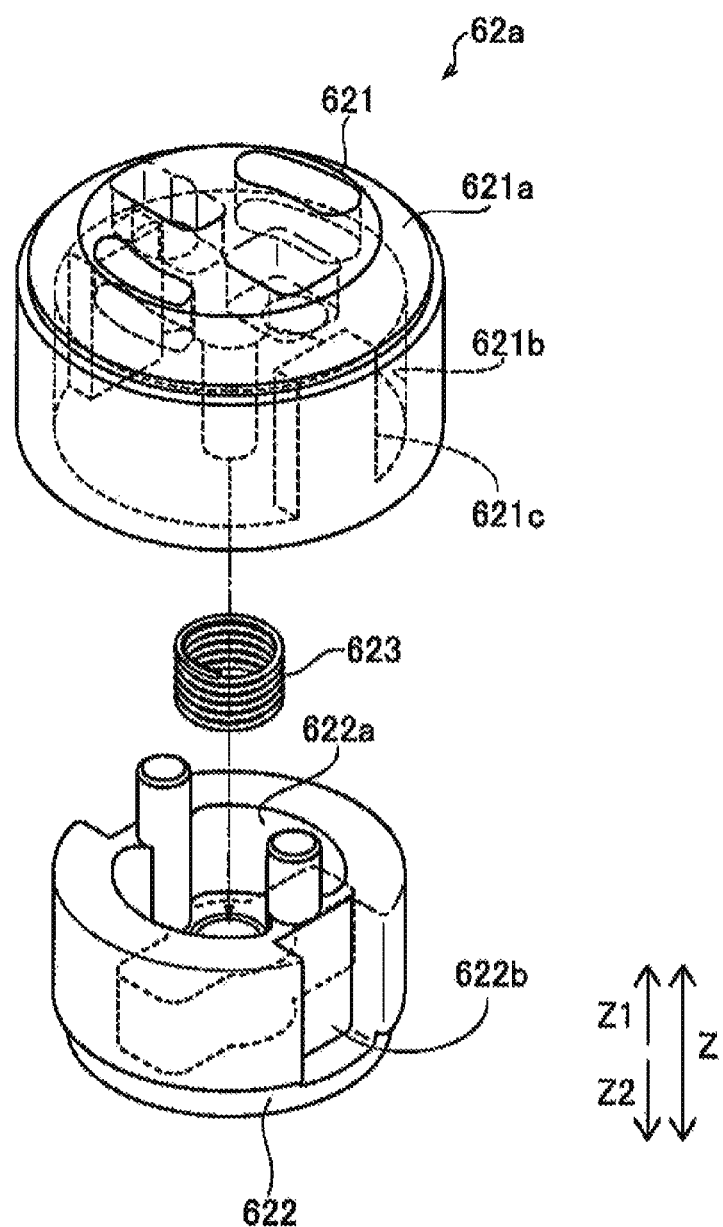
FIG. 8 is a diagram illustrating an exploded perspective view of a drive transmission member of the adaptor according to an embodiment.

As illustrated in FIG. 8, each drive transmission member 62a includes a first member 621 and a second member 622. The second member 622 is provided movably with respect to the first member 621 with a bias member 623 interposed in between. The first member 621 includes a recess portion 621b and an engagement portion 621c. The recess portion 621b receives the second member 622 fitted thereto. The engagement portion 621c is engaged with the second member 622. The second member 622 includes a recess portion 622a and an engagement portion 622b. The recess portion 622a accommodates the bias member 623. The engagement portion 622b is engaged with the first member 621. The first member 621 and the second member 622 are fitted to each other in the Z direction with the bias member 623 interposed in between. The first member 621 is positioned in the second surface 60b side (the Z1 side) with respect to the second member 622. The second member 622 is positioned in the first surface 60a side (the Z2 side). The bias member 623 biases the first member 621 toward the Z1 side with respect to the second member 622. For example, the bias member 623 is configured as a compress coil spring. Note that the drive transmission member 62b has the configuration same as the drive transmission member 62b except for the shape of a portion where the transmission member is engaged with the driven member 44 of the surgical instrument 40. Note that the bias member 623 is an example of a second bias member.

The first member 621 is arranged movably with respect to the base body 61 in the Z direction. This makes it possible to move the first member 621 of each of the drive transmission members 62b and 62a downward in the Z direction to prevent interference with the movement of the surgical instrument 40 when attaching the surgical instrument 40 to the adaptor 60 while guiding the surgical instrument 40 along the pair of guide rails 63. Specifically, the pair of guide grooves 45 are configured to guide the pair of guide rails 63 in a direction (the Y direction) crossing a direction (the Z direction) in which the driven members 44a and 44b are engaged with the drive transmission members 62b and 62a. In this case, the first member 621 of each of the drive transmission member 62a and 62b can be moved so as not to obstruct the movement of the surgical instrument 40 when attaching the surgical instrument 40 to the adaptor 60 while guiding the surgical instrument 40 along the guide rails 63.

The first member 621 is configured to rotate in accordance with the rotation of the second member 622 about the rotation axis in the Z direction. Specifically, the first member 621 and the second member 622 are configured such that the engagement portion 621c provided on an inner circumference of the first member 621 and the engagement portion 622b provided on an outer circumference of the second member 622 are engaged with each other. The engagement portion 621c of the first member 621 is formed to protrude inward from the recess portion 621b. The engagement portion 622b of the second member 622 is formed to be recessed inward from the outer circumference of the second member 622. The engagement portion 621c of the first member 621 and the engagement portion 622b of the second member 622 are configured to be engaged with each other even when the first member 621 is moved with respect to the second member 622 in the Z direction. Specifically, the first member 621 is configured to be rotated with the second member 622 regardless of a location of the first member 621 with respect to the second member 622 in the Z direction. Therefore, when the second member 622 is rotated in accordance with the rotation of the rotation drive part 212 of the robot arm 21a, the first member 621 is rotated together. Consequently, the rotations of the rotation drive parts 212 of the robot arm 21a are transmitted to the driven members 44a and 44b of the surgical instrument 40 engaged with the first members 621 of the drive transmission members 62a and 62b.

(Configuration of Movable Member)

Figure 9:
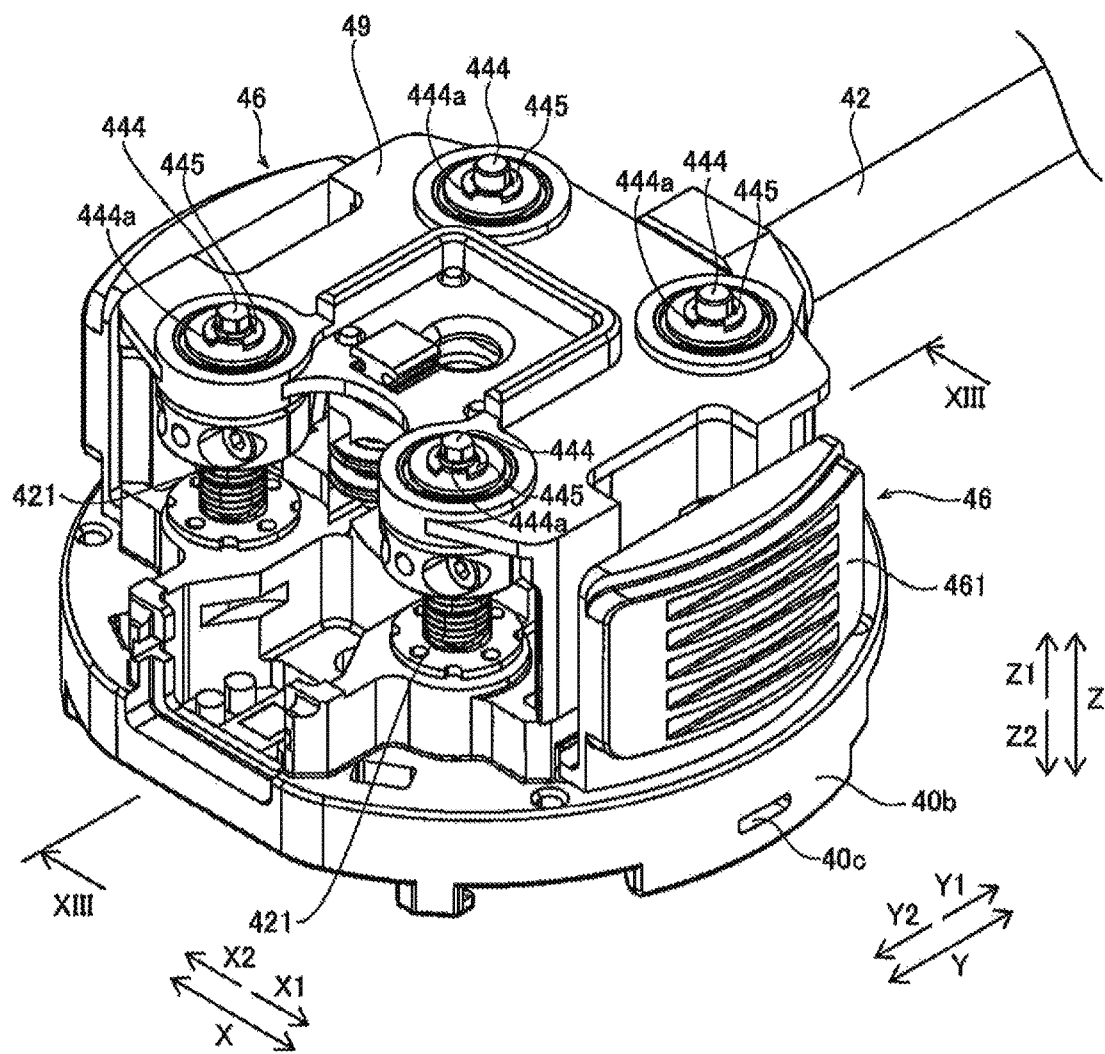
FIG. 9 is a diagram illustrating a perspective view of an inside of a housing of the surgical instrument according to an embodiment.
Figure 10:
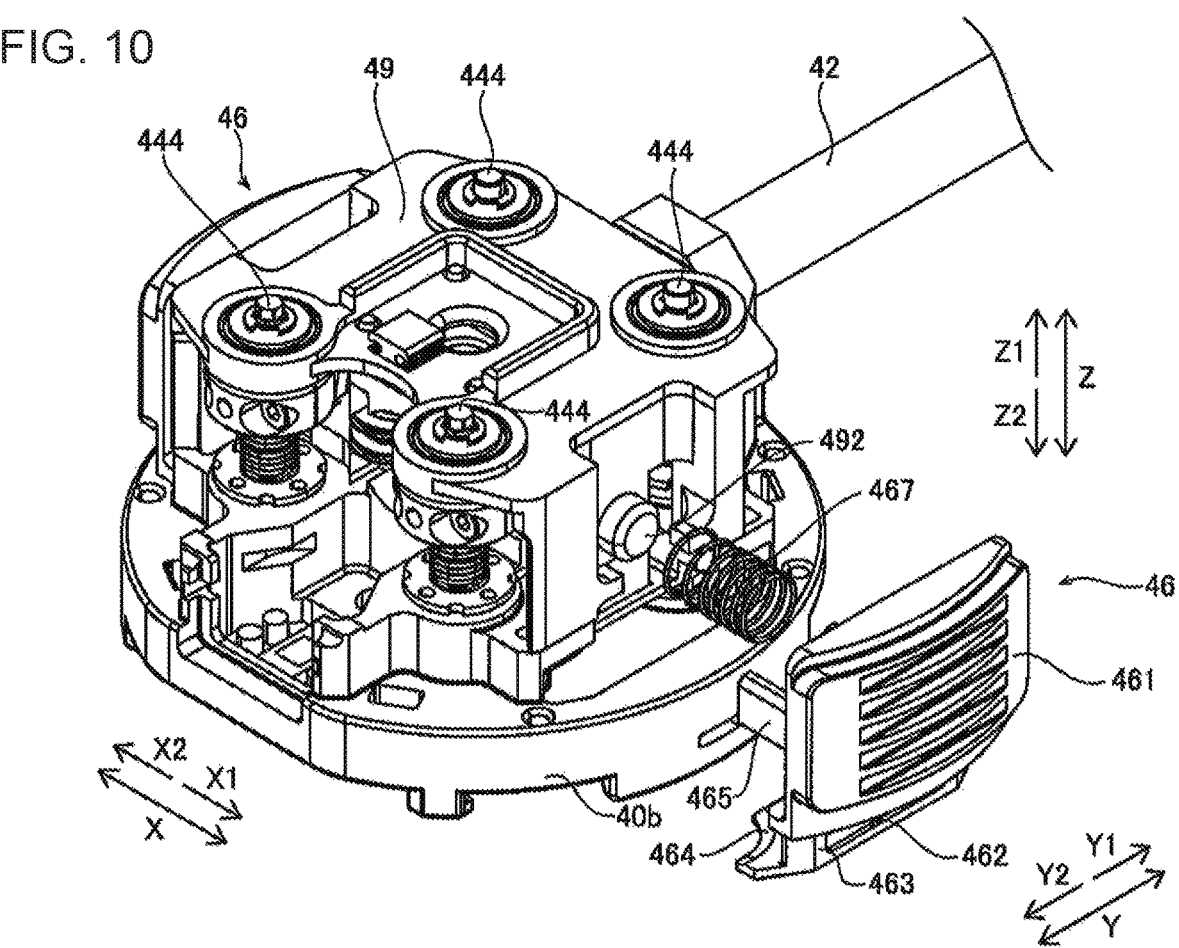
FIG. 10 is a diagram illustrating an exploded perspective view of a state where a movable member is detached from a base body of the surgical instrument according to an embodiment.
Figure 11:
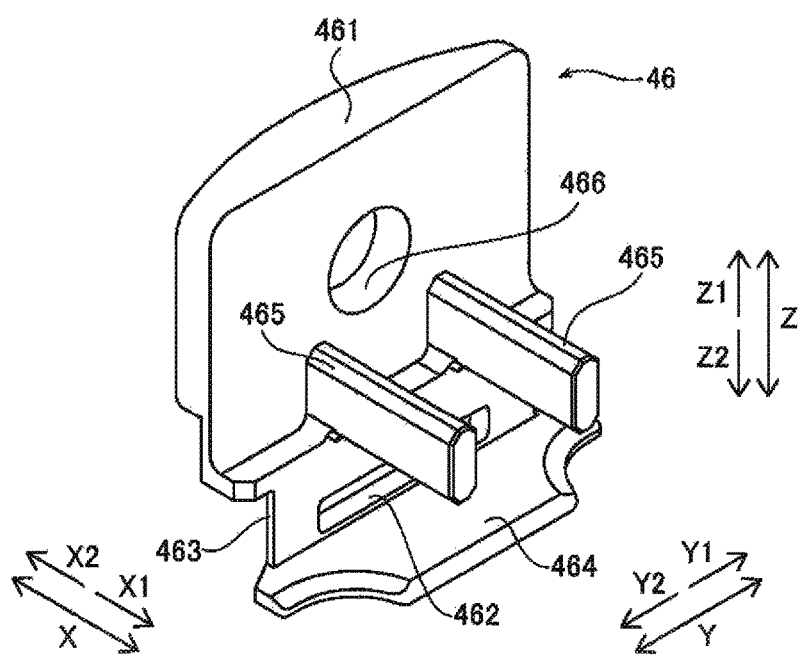
FIG. 11 is a diagram illustrating a perspective view of a movable member of the surgical instrument according to an embodiment.
Figure 15:
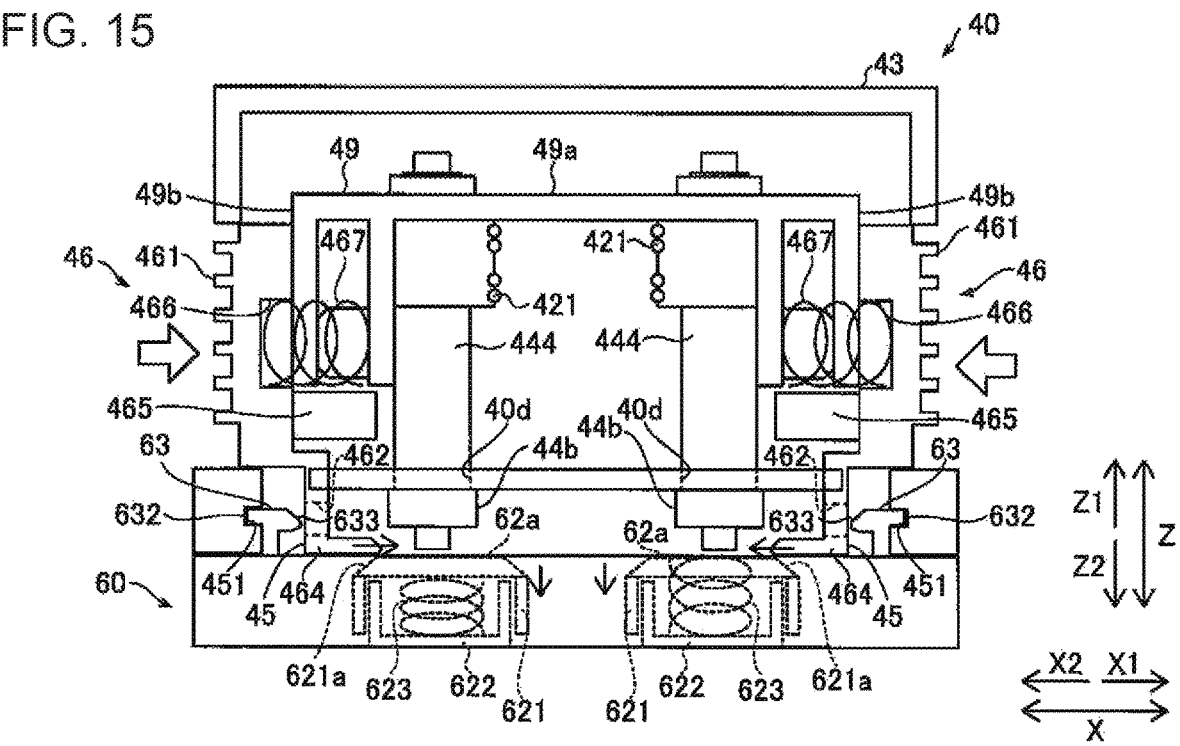
FIG. 15 is a diagram illustrating a second explanatory view for explaining the movement of the movable member of the surgical instrument according to an embodiment.

As illustrated in FIGS. 9 to 11, each of the movable members 46 of the surgical instrument 40 includes a pressing portion 461 (button portion), the engagement hole 462, the side wall 463, a press-down portion 464, a pair of guide portions 465, and a recessed portion 466. The movable members 46 are attached to the base body 40b and the holding member 49 with sandwiching a bias member 467 between the holding member 49 and each of the movable members 46. As illustrated in FIGS. 14 and 15, the movable members 46 are biased in directions (outward directions) in which the widths of the guide grooves 45 are decreased by the bias members 467. The movable members 46 are moved in directions (inward directions) in which the widths of the guide grooves 45 are increased when the worker presses the pressing portion 461. Specifically, the movable member 46 on the X1 side is biased in the X1 direction by the corresponding bias member 467. The movable member 46 on the X1 side is moved in the X2 direction against the bias force by being pressed toward the X2 side. On the other hand, the movable member 46 on the X2 side is biased in the X2 direction by the corresponding bias member 467. The movable member 46 on the X2 side is moved in the X1 direction against the bias force by being pressed toward the X1 side. Note that the engagement hole 462 is an example of an engagement portion. The bias member 467 is an example of a first bias member.

The pair of the movable members 46 are arranged in a direction (the X direction) substantially orthogonal to the extending direction of the shaft 42. Thus, the pair of the movable members 46 are engaged with the adaptor 60 to fix the surgical instrument 40 in a well-balanced manner. Therefore, the surgical instrument 40 can be more stably fixed to the adaptor 60.

The pressing portion 461 is provided to be pressed (operated) by the worker. As illustrated in FIG. 5, the pressing portion 461 is provided on the outer side in the X direction so as to be exposed from the housing 43. The pressing portion 461 is formed with a plurality of grooves extending along the Y direction. This makes it possible to recognize the pressing portion 461 only by touching the position of the pressing portion 461 and also to suppress slipping of the hand of the operator.

The engagement hole 462 is engaged with the tab portion 633 provided on the guide rail 63 of the adaptor 60. As illustrated in FIG. 11, the engagement hole 462 is formed in the side wall 463. As illustrated in FIGS. 14 and 15, the engagement hole 462 is formed to penetrate through the side wall 463 in the X direction. This allows the positioning and fixing to the adaptor 60 of the surgical instrument 40 that is guided by the guide rails 63.

As illustrated in FIG. 15, the movable members 46 are configured to be disengaged from the adaptor 60 by moving the movable members 46 with respect to the base body 40b and the holding member 49. Accordingly, by engaging the movable members 46 to the adaptor 60, the surgical instrument 40 can be easily attached to the adaptor 60 and can be stably fixed to the adaptor 60. Further, by moving the movable members 46 with respect to the base body 40b and the holding member 49, the engagement between the movable members 46 and the adaptor 60 can be released. Thus, the surgical instrument 40 can be easily detached from the adaptor 60. Therefore, the surgical instrument 40, which is to be detachably connected to the robot arm 21a of the robotic surgical system 100 through the adaptor 60, can be easily attached to and detached from the adaptor 60 and can be stably fixed to the adaptor 60.

The side wall 463 constitutes an inner wall in the X direction of the guide groove 45. Specifically, as illustrated in FIGS. 14 and 15, the side wall 463 is arranged to face the restriction portion 451 provided on the base body 40b. The guide groove 45 defined by the side wall 463 and the restriction portion 451 sandwiches the rail portion 631 of the guide rail 63 to guide the guide rail 63.

The restriction portion 451 is provided on the base body 40b side in the guide groove 45. The restriction portion 451 is formed to extend in the Y direction. The restriction portion 451 is engaged with the jut portion 632 provided on the guide rail 63 and projected in the direction (the X direction) parallel to the attachment surface 40a, and restricts the movement of the attachment surface 40a with respect to the adaptor 60 in the direction (the Z direction) of the rotation axis of the driven members 44a and 44b.

As illustrated in FIGS. 14 and 15, when the press-down portion 464 is moved to release the engagement of the engagement hole 462 with the adaptor 60, the press-down portion 464 disengages the drive transmission member 62a (62b) from the driven member 44b (44a) by moving the first member 621 of the drive transmission member 62a (62b) in the direction away from the driven member 44b (44a). With this configuration, the operation of releasing the engagement of the movable members 46 with the adaptor 60 and the operation of releasing the engagement of the driven members 44b (44a) with the drive transmission members 62 can be performed at the same time. Consequently, it is possible to detach the surgical instrument 40 from the adaptor 60 easily.

Specifically, the press-down portion 464 is configured to disengage the drive transmission members 62a (62b) from the driven members 44b (44a) by being moved in the direction (the X direction) crossing the direction in which the driven members 44b (44a) are engaged with the drive transmission members 62a (62b), along with the movement of the movable member 46.

Specifically, the press-down portion 464 is configured, along with the movement of the movable member 46, to run onto tapered portion 621a of the first member 621 and to move the first member 621 in the direction (the Z2 direction) away from the driven member 44b (44a).

The press-down portion 464 is connected to an inner side in the X direction of the Z2 side portion of the side wall 463. The press-down portion 464 is formed in a plate shape extending in the XY plane. The press-down portion 464 includes recesses in portions corresponding to the driven member 44b (44a).

Figure 13:
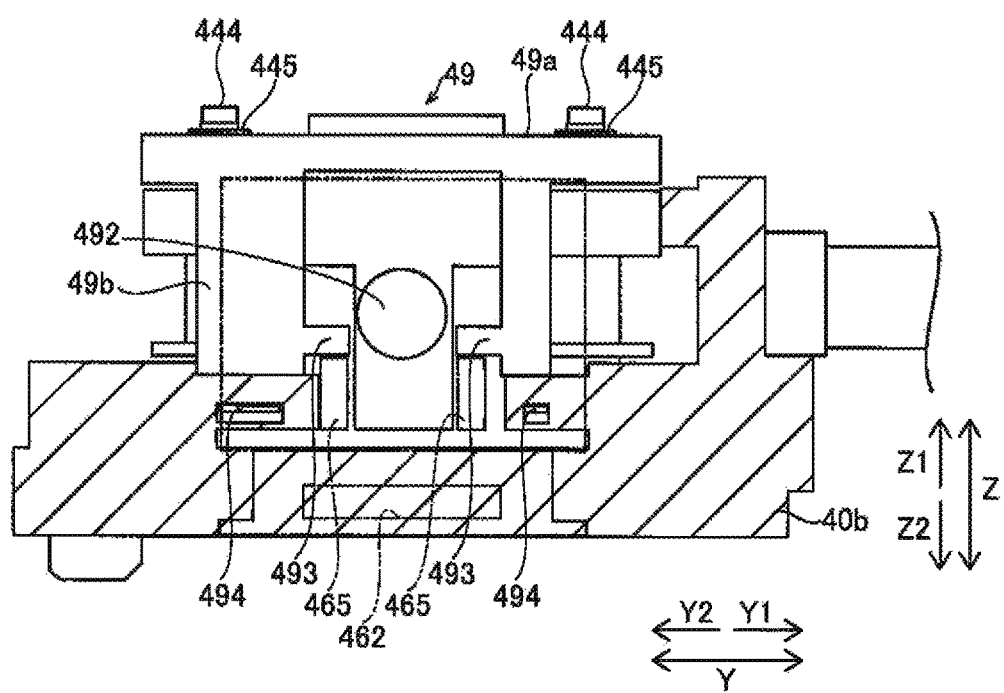
FIG. 13 is a diagram illustrating a cross sectional view along the XIII-XIII line in FIG. 9.

The pair of guide portions 465 are configured to guide the movement of the movable members 46 in the X direction. The pair of guide portions 465 are arranged side by side in the Y direction. The pair of guide portions 465 are formed to extend in the X direction. Specifically, each of the pair of guide portions 465 extends inwardly from the inner surface of the pressing portion 461. As illustrated in FIG. 13, the movement of the guide portion 465 is restricted in an upper direction by the holding member 49 and in a lower direction by the base body 40b.

The recessed portion 466 is configured such that the bias member 467 is fit into the recessed portion 466. The recessed portion 466 is provided to be recessed outwardly from the inner surface of the pressing portion 461. The recessed portion 466 is provided in the vicinity of the center in the Z direction of the pressing portion 461. The recessed portion 466 is provided in the vicinity of the center in the Y direction of the pressing portion 461. With this, the biasing force of the bias member 467 acts on the center of the pressing portion 461.

The bias member 467 biases the movable member 46 toward an outer direction of the base body 40b. The inner end of the bias member 467 is retained by the holding member 49. Accordingly, the movement of the bias member 467 toward the inner side along the X direction is restricted. As a result, the bias member 467 can be held by the holding member 49 which holds the driven member 44b (44a). Thus, it is not necessary to additionally provide a dedicated member for holding the bias member 467. Therefore, it is possible to suppress an increase in the number of components. The outer end of the bias member 467 is fit in the recessed portion 466 provided on the inner surface of the pressing portion 461. For example, the bias member 467 is configured as a compression coil spring.

As illustrated in FIG. 9, the base body 40b is provided with an opening 40c which communicates with the engagement hole 462 from the outside of the base body 40b. Therefore, even when it is difficult to operate the pressing portion 461, an operation to move the engagement hole 462 can be done through the opening 40c so as to release the engagement of the engagement hole 462 with the adaptor 60.

(Configuration of Holding Member)

Figure 12:
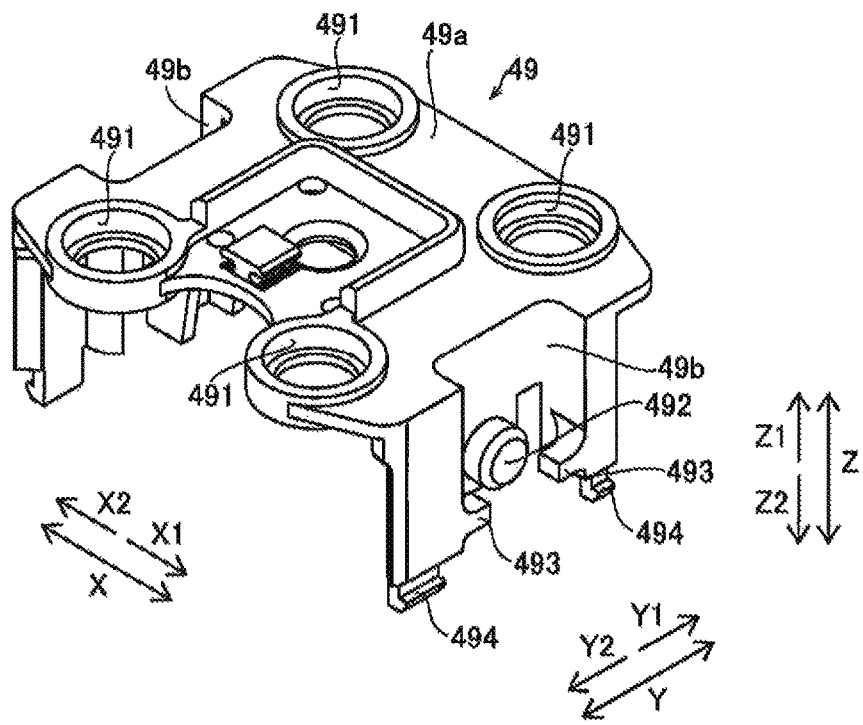
FIG. 12 is a diagram illustrating a perspective view of a holding member of the surgical instrument according to an embodiment.

As illustrated in FIG. 12, the holding member 49 of the surgical instrument 40 includes an upper surface 49a and a pair of side surfaces connected to the upper surface 49a. The upper surface 49a of the holding member 49 is formed with support portions 491 that rotatably support the driven members 44a and 44b, respectively. Each of the side surfaces 49b of the holding member 49 is formed with a projection 492, restriction portions 493, and claws 494. The holding member 49 is made of resin.

Each of the driven member 44a and 44b includes one end (the Z2 side end) to be rotatably supported by the base body 40b and the other end (the Z1 side end) to be rotatably supported by the holding member 49. The holding member 49 is configured to rotatably support the other end (the Z1 side end) of each of the plural driven members 44a and 44b. Specifically, as illustrated in FIG. 13, the holding member 49 is engaged with the base body 40b and holds the end of each of the driven members 44a and 44b with a retaining ring 445 such an e-ring or the like, so that the holding member 49 is fixed to the base body 40b. With this, the holding member 49 can be stably fixed to the base body 40b. Thus, the driven members 44a and 44b can be stably held by the holding member 49.

More specifically, a rotational shaft 444 of each of the driven members 44a (44b) is inserted into a through hole 40d (see FIG. 14) of the base body 40b from the Z2 side with a bearing therebetween. Then, a member around which the wire 421 is to be wound is attached to the rotational shaft 444, and the wire 421 is attached to the member attached to the rotational shaft 444. After that, the holding member 49 is engaged with the base body 40b. Specifically, the plural claws 494 of the holding member 49 are engaged with the base body 40b by snap fit. At this time, the Z1 side end of each of the driven members 44a (44b) is inserted into the support portion 491 of the holding member 49 with a bearing therebetween. Then, the retaining ring 445 serving as a fastener or an attachment is fit to a groove 444a provided on an outer circumference of the shaft 444 of each of the driven members 44a (44b), so that the end of each of driven members 44a and 44b is held by the holding member 49. Therefore, the holding member 49 is fixed to the base body 40b and the Z1 side end of each of the driven members 44a (44b) is rotatably supported by the holding member 49.

The support portions 491 are provided at positions corresponding to the positions of the driven members 44a and 44b. Each of the support portions 491 is formed with a through hole penetrating therethrough in the Z direction. Each of the support portions 491 is configured to rotatably hold the end (Z1 side end) of each of the did plural driven members 44a and 44b whose other end (the Z2 side end) is supported by the base body 40b.

The projection 492 of the holding member 49 is projected outwardly toward the movable member 46 side. The bias member 467 is attached to the projection 492 such that the projection 492 is inserted into the bias member 467. Accordingly, by the projection 492 provided on the holding member 49, the bias members 467 can be easily held.

The restriction portions 493 of the holding member 49 restrict the movements of the guide portions 465 of the movable member 46 in the Z1 direction.

The plural claws 494 of the holding member 49 are engaged with the base body 40b by snap fit.

(Attachment of Surgical Instrument to Robot Arm)

Figure 16:
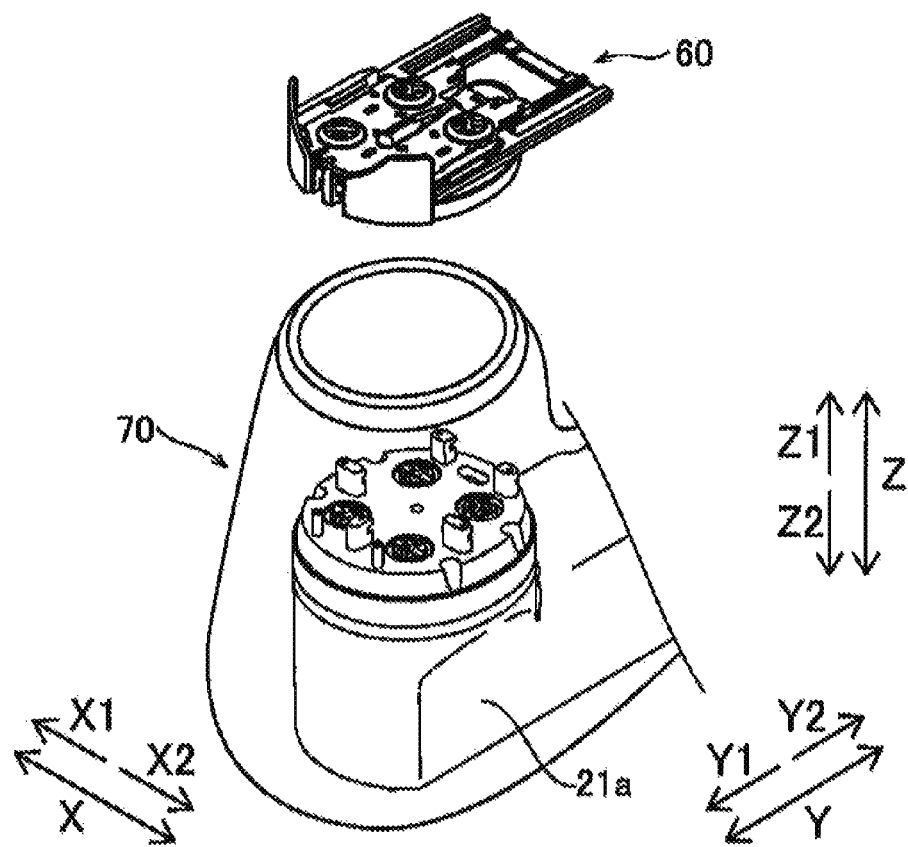
FIG. 16 is a diagram illustrating a first explanatory view for explaining attachment of the adaptor to the robot arm according to an embodiment.
Figure 17:
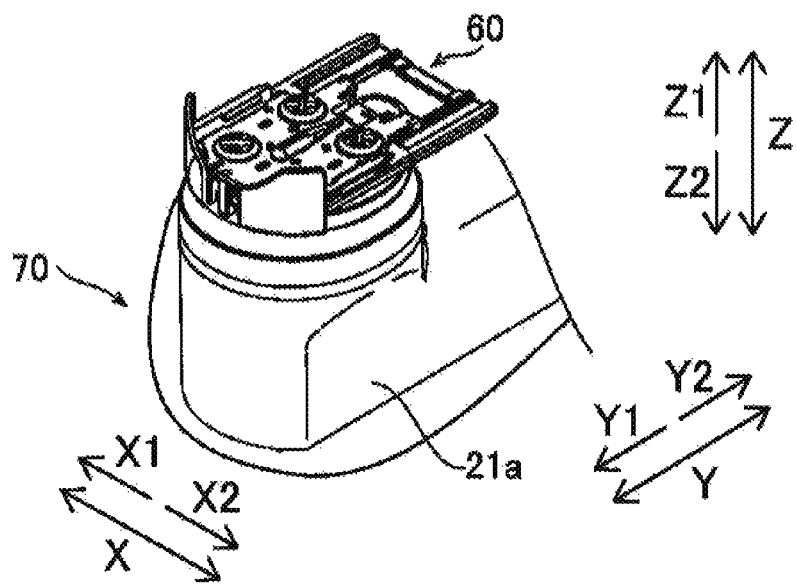
FIG. 17 is a diagram illustrating a second explanatory view of attachment of the adaptor to the robot arm according to an embodiment.
Figure 18:
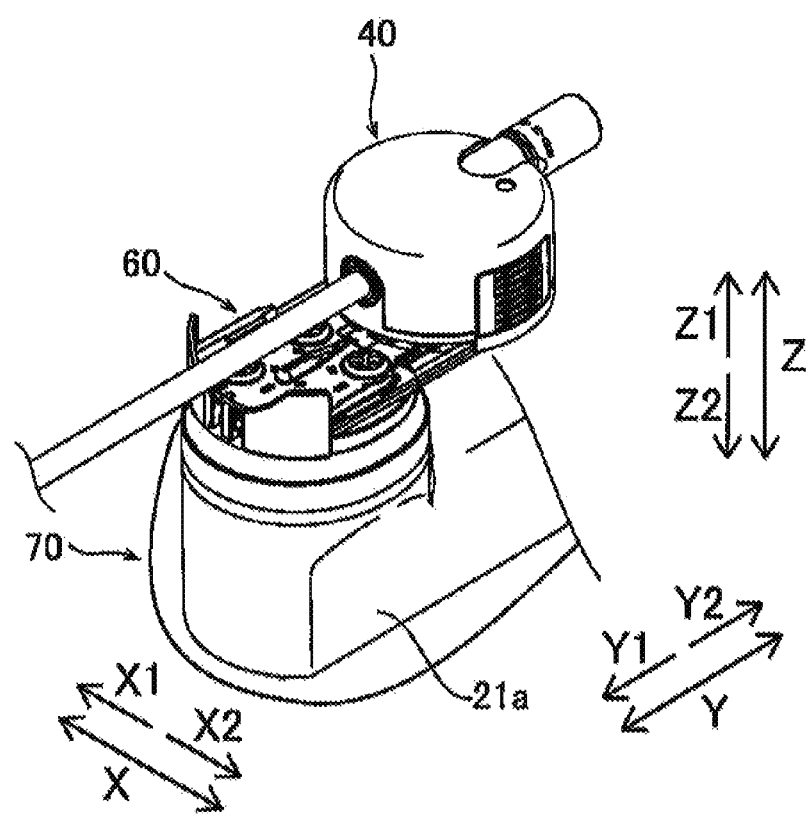
FIG. 18 is a diagram illustrating an explanatory view for explaining the attachment of the surgical instrument to the adaptor according to an embodiment.

With reference to FIGS. 16 to 18, attachment of the surgical instrument 40 to the robot arm 21a according to an embodiment is described.

As illustrated in FIGS. 16 and 17, the adaptor 60 is attached to the robot arm 21a with the robot arm 21a being covered by the drape 70. The adaptor 60 is moved in the Z direction with respect to the robot arm 21a, so as to be attached to the robot arm 21a. As illustrated in FIG. 18, the surgical instrument 40 is attached to the adaptor 60 attached to the robot arm 21a. The surgical instrument 40 is moved in the Y1 direction along the guide rails 63 of the adaptor 60, so as to be attached to the adaptor 60. In this way, the surgical instrument 40 is attached to the robot arm 21a through the adaptor 60.

When detaching the surgical instrument 40 from the robot arm 21a, a user slides the surgical instrument 40 in the Y2 direction while pressing the pressing portions 461 of the movable members 46 of the surgical instrument 40, to detach the surgical instrument 40 from the adaptor 60.

(Modifications)

It should be understood that one or more embodiments described above are illustrated by way of example in every respect and not limit the disclosure. The scope of the disclosure is defined not by one or more embodiments described above, but by the scope of claims, and includes all modifications (variations) within equivalent meaning and scope to those of the claims.

For example, in one or more embodiments described above, the surgical instrument is attached or detached by being slid in the extending direction of the shaft along the second surface of the adaptor. However, the disclosure is not limited thereto. In this disclosure, a surgical instrument may be attached or detached by being slid in a direction crossing an extending direction of a shaft along a second surface of an adaptor.

Further, in one or more embodiments described above, the guide groove is defined by the movable member and the based body. However, the disclosure is not limited thereto. In this disclosure, a guide groove to slidably receive a guide rail provided at an adaptor may be formed by at least a movable member.

Further, in one or more embodiments described above, the movable member is movable in the direction crossing the extending direction of the shaft. However, the disclosure is not limited thereto. In this disclosure, a movable member may be movable in a direction along an extending direction of a shaft. Further, a movable member may be movable in a direction along a rotational axis of a driven member.

Further, in one or more embodiments described above, the attachment surface of the surgical instrument is formed in a substantially circular shape in the plan view. However, the disclosure is not limited thereto. In this disclosure, an attachment surface of a surgical instrument may not be formed in a substantially circular shape in a plan view. For example, an attachment surface of a surgical instrument may be formed in a rectangular shape in a plan view.

Further, in one or more embodiments described above, the four driven members are provided on the base body of the surgical instrument. However, the disclosure is not limited thereto. In this disclosure, the number of a plurality of driven members provided on a base body of a surgical instrument may be other than four.

In one or more embodiments described above, the adaptor and drape are separately provided. However, the disclosure is not limited thereto. In this disclosure, an adaptor and a drape may be integrally provided.

The invention claimed is:

1. A surgical instrument to be detachably connected to a robot arm of a robotic surgical system through an adaptor, comprising:
    a base body including an attachment surface to be attached to the adaptor;
    an elongated shaft including one end connected to the base body and the other end;
    a treatment tool provided on a side of the other end of the elongated shaft;
    elongate elements for operating the treatment tool;
    driven members rotatably provided on the base body and connected with end portions of the elongate elements;
    a holding member rotatably holding the driven members such that one end of each of the driven members is rotatably held by the base body and the other end of each of the driven members is rotatably held by the holding member; and
    a movable member provided with being movable with respect to the holding member and the base body and engaged with the adaptor, wherein
    the movable member is configured to be disengaged from the adaptor, when the movable member is moved with respect to the holding member and the base body.

2. The surgical instrument according to claim 1, wherein the movable member defines at least partially a guide groove that slidably receives a guide rail provided to the adaptor, and
    the movable member is configured to change a groove width of the guide groove when the movable member is moved.

3. The surgical instrument according to claim 1, further comprising
    a first bias member biasing the movable member toward an outer periphery of the base body, wherein
    the first bias member is held by the holding member.

4. The surgical instrument according to claim 3, wherein
    the holding member includes a projection projected toward the movable member,
    the first bias member comprises a compression coil spring, and
    the compression coil spring is inserted to the projection.

5. The surgical instrument according to claim 1, wherein
    the holding member is engaged with the base body and holds the other end of each of the driven members with an attachment.

6. The surgical instrument according to claim 5, wherein the attachment comprises a retaining ring.

7. The surgical instrument according to claim 6, wherein
    each of the driven members includes a shaft including an outer circumference formed with a groove, and
    the holding member holds the other end of each of the driven members by the retaining ring being fit in the groove of the shaft of each of the driven members.

8. The surgical instrument according to claim 1, wherein
    the movable member includes a pressing portion to be pressed and an engagement portion to be engaged with the adaptor, and
    the base body includes an opening through which the engagement portion is accessible from the outside of the base body.

9. The surgical instrument according to claim 8, wherein the engagement portion of the movable member includes an engagement hole to be engaged with a claw provided to the adaptor.

10. The surgical instrument according to claim 1, wherein
    the adaptor includes drive transmission members each of which includes a first member and a second member provided movably with respect to the first member with a second bias member interposed therebetween, the drive transmission members being provided to be engaged with the driven members, and
    the movable member includes a press-down portion configured to, when the movable member is moved to disengage the movable member from the adaptor, move the first members of the drive transmission members in a direction away from the driven members so as to disengage the drive transmission members from the driven members.

11. The surgical instrument according to claim 1, wherein the movable member comprises a pair of movable members arranged in a direction substantially orthogonal to an extending direction of the elongated shaft.

12. Assembly comprising:
    an adaptor that is to be attached to a robot arm of a robotic surgical system; and
    a surgical instrument detachably connected to the adaptor, wherein
    the surgical instrument includes:
    a base body including an attachment surface to be attached to the adaptor;
    an elongated shaft including one end connected to the base body and the other end;
    a treatment tool provided on a side of the other end of the elongated shaft;

elongate elements for operating the treatment tool;
driven members rotatably provided on the base body and connected with end portions of the elongate elements;
a holding member rotatably holding the driven members such that one end of each of the driven members is rotatably held by the base body and the other end of each of the driven members is rotatably held by the holding member; and
a movable member provided with being movable with respect to the holding member and the base body and engaged with the adaptor, wherein
the movable member is configured to be disengaged from the adaptor, when the movable member is moved with respect to the holding member and the base body.

13. The assembly according to claim 12, wherein
the adaptor includes a pair of guide rails,
the attachment surface of the surgical instrument includes a pair of guide grooves to slidably receive the pair of guide rails, and
groove widths of the guide grooves are changed when the movable member is moved.

14. The assembly according to claim 12, wherein
the surgical instrument includes a first bias member biasing the movable member toward an outer periphery of the base body, and
the first bias member is held by the holding member.

15. The assembly according to claim 14, wherein
the holding member includes a projection projected toward the movable member,
the first bias member comprises a compression coil spring, and
the compression coil spring is inserted to the projection of the holding member.

16. The assembly according to claim 12, wherein
the holding member is engaged with the base body and holds the other end of each of the driven members with an attachment.

17. The assembly according to claim 13, wherein
each of the pair of guide rails includes a rail portion extending in a first direction and a claw projected from the rail portion in a second direction substantially orthogonal to the first direction,
the movable member includes a pressing portion to be pressed and an engagement portion to be engaged with the adaptor, and
the engagement portion includes an engagement hole to be engaged with the claw.

18. The assembly according to claim 12, wherein
the adaptor includes drive transmission members each of which includes a first member and a second member provided movably with respect to the first member with a second bias member interposed therebetween, the drive transmission members being provided to be engaged with the driven members of the surgical instrument, and
the movable member includes a press-down portion configured to, when the movable member is moved to disengage the movable member from the adaptor, move the first members of the drive transmission members in a direction away from the driven members so as to disengage the drive transmission members from the driven members.

19. A robotic surgical system, comprising:
a robot arm;
an adaptor attached to the robot arm; and
a surgical instrument detachably connected to the adaptor, wherein
the surgical instrument includes:
a base body including an attachment surface to be attached to the adaptor;
an elongated shaft including one end connected to the base body and the other end;
a treatment tool provided on a side of the other end of the elongated shaft;
elongate elements for operating the treatment tool;
driven members rotatably provided on the base body and connected with end portions of the elongate elements;
a holding member rotatably holding the driven members such that one end of each of the driven members is rotatably held by the base body and the other end of each of the driven members is rotatably held by the holding member; and
a movable member provided with being movable with respect to the holding member and the base body and engaged with the adaptor, and
the movable member is configured to be disengaged from the adaptor, when the movable member is moved with respect to the holding member and the base body.

20. The robotic surgical system according to claim 19, wherein
the adaptor is a drape adaptor that sandwiches a drape between the adaptor and the robot arm.

* * * * *